United States Patent [19]

Arakawa

[11] Patent Number: 5,591,498
[45] Date of Patent: Jan. 7, 1997

[54] STRUCTURE OF RELEASING PART

[75] Inventor: Masaaki Arakawa, Osaka, Japan

[73] Assignee: Nitto Denko Corporation, Osaka, Japan

[21] Appl. No.: 63,739

[22] Filed: May 20, 1993

[30] Foreign Application Priority Data

Jun. 5, 1992 [JP] Japan .................................. 4-171925

[51] Int. Cl.$^6$ ...................... B32B 7/00; A61F 13/60
[52] U.S. Cl. ...................... 428/40.1; 428/41.5; 428/41.8; 428/343; 428/352; 604/390
[58] Field of Search ................ 428/40, 343, 352, 428/355, 356, 411.1, 447, 451, 492, 40.1, 41.5, 41.8; 604/389, 390

[56] References Cited

U.S. PATENT DOCUMENTS

| | | | |
|---|---|---|---|
| 3,797,495 | 3/1974 | Schmidt | 604/390 |
| 4,594,277 | 6/1986 | Galli et al. | 428/40 |
| 4,699,816 | 10/1987 | Galli | 428/40 |
| 5,112,889 | 5/1992 | Miller et al. | 524/77 |
| 5,198,476 | 3/1993 | Kobayashi et al. | 522/31 |
| 5,229,179 | 7/1993 | Kumar et al. | 428/40 |
| 5,264,281 | 11/1993 | Arakawa et al. | 428/354 |
| 5,306,758 | 4/1994 | Pellerite | 524/366 |
| 5,342,339 | 8/1994 | Carpenter et al. | 604/385.1 |

FOREIGN PATENT DOCUMENTS

| | | |
|---|---|---|
| 0458581 | 11/1991 | European Pat. Off. . |
| 0478512 | 4/1992 | European Pat. Off. . |
| 0510200 | 10/1992 | European Pat. Off. . |
| 0519086 | 12/1992 | European Pat. Off. . |

OTHER PUBLICATIONS

WO92/07042 published Apr. 30, 1992 (Japanese language) and English language translation thereof.

*Primary Examiner*—Patrick Ryan
*Assistant Examiner*—Marie R. Yamnitzky
*Attorney, Agent, or Firm*—Sughrue, Mion, Zinn, Macpeak & Seas

[57] ABSTRACT

A releasing part structure having a boundary component which is constituted by a pressure-sensitive adhesive layer and a long chain alkyl type or silicone type releasing agent layer, wherein said pressure-sensitive adhesive layer comprises a pressure-sensitive adhesive composition comprising a rubber-based or acrylic pressure-sensitive adhesive, and the releasing part structure is constituted such that when the pressure-sensitive adhesive layer is released from the releasing agent layer, the sound pressure level in releasing the pressure-sensitive adhesive layer from the releasing agent layer at a releasing speed of at least $1\times10^2$ mm/minute is 80 dB or less.

4 Claims, 4 Drawing Sheets

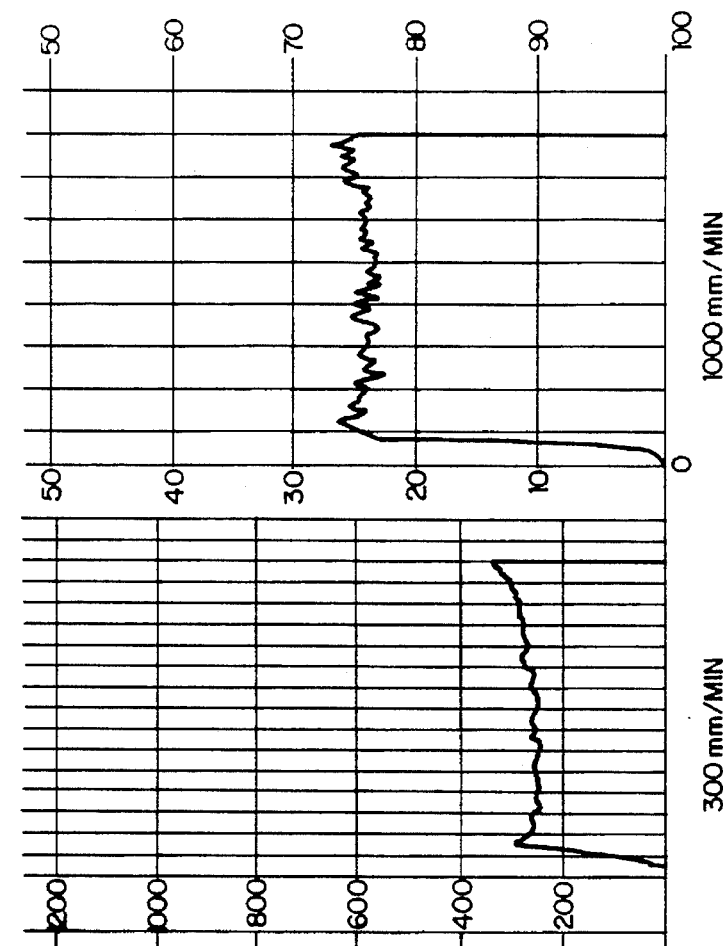

STRUCTURE OF RELEASING PART

FIELD OF THE INVENTION

The present invention relates to a structure of a releasing part giving a reduced releasing noise and the object thereof is to provide a releasing part which is used as the releasing parts of living commodities and, practically, the releasing part of an adhesive tape mainly for, e.g., a paper diaper, in which a fastener tape is releasably adhered and fixed to back surfaces of a reinforcing film and a releasing tape although there is no restriction on the use of the releasing part structure of the present invention. Furthermore, the present invention is also suitably used as the structure of a releasing part which is utilized for other disposable absorbing articles such as sanitary napkins as well as the structure of a releasing part in various living commodoties such as medical tapes, packing tapes, etc.

In general, it is required in the structure of a diaper releasing part in which a tape for a diaper, such as a fastener tape, is fixed, that the fastener tape is reluctant to detach at fixing for preventing leakage or slippage during wearing the diaper, and on the other hand, it is required in the structure that the fastener tape is easily released from the diaper in order that the diaper be put on and off easily.

For those reasons, in the fastener part of a diaper, an adhesive easily giving high adhesion has hitherto been used as the adhesive for the fastener tape, or a reinforcing film is formed on the front part of the diaper to faciliate releasing, and a long chain alkyl type releasing agent having a high holding property is coated on the reinforcing film to prevent the fastener tape from being released from the reinforcing film at fixing.

The long chain alkyl type releasing agent exhibits its advantage as an excellent releasing agent for meeting the above-described requirement but on the other hand, there is a disadvantage that when mother tries to release the fastener tape from the reinforcing film, the tape is released with a loud noise of "Bari—Bari".

Such a releasing noise causes a problem of awaking the baby in sleep or awaking sleeping persons around the sleeping baby, and hence the improvement in this respect has been desired.

On the other hand, when silicone type releasing agent which is generally used as a releasing agent for adhesive tapes, etc., is used for the fastener tape, the tape does not make such a noise and the chart pattern of the releasing force becomes smooth.

However, since use of the silicone type releasing agent extremely reduces a shear adhesive strength to the adhesive layer of the tape, there is a disadvantage that the tape is liable to release in the case of using the tape for the fastener part of a diaper, and hence the silicone type releasing agent is used little for such a fixing use at present.

The inventors previously provided a releasing part structure having both a noiseless property and a high holding property by incorporating a three-dimensional organopolysiloxane in the above-described silicone type releasing agent to impart a heavy releasing property to the releasing part structure as described in JP-A-5-17728. (The term "JP-A" as used herein means an "unexamined published Japanese patent application").

However, in the above-described technique, too heavy of a release results, whereby a sufficient noiseless effect is not obtained.

SUMMARY OF THE INVENTION

As a result of investigations to further improve the conventional noiseless releasing property in view of the above-described problems, it has been found that the desired object can be achieved by specifying the relationship between, in particular, the releasing speed and releasing force and the releasing noise in the case of releasing the pressure-sensitive adhesive layer from the releasing layer. The present invention has been attained based on this finding.

Accordingly, an object of the present invention is to provide a structure of a releasing part the boundary of which is constituted by a pressure-sensitive adhesive layer and a long chain alkyl type or silicone type releasing agent layer, wherein the adhesive layer comprises a pressure-sensitive adhesive composition comprising a rubber-based or acrylic pressure-sensitive adhesive, and the releasing part stucture is constituted such that when the pressure-sensitive adhesive layer is released from the releasing agent layer, a sound pressure level in releasing at a releasing speed of at least $1\times10^2$ mm/minute is 80 dB or less.

BRIEF DESCRIPTION OF THE DRAWINGS

FIG. 8 is a graph of the pattern showing the back surface releasing force chart in the various releasing speeds in Example 1 of the present invention.

DETAILED DESCRIPTION OF THE INVENTION

Figure 1:
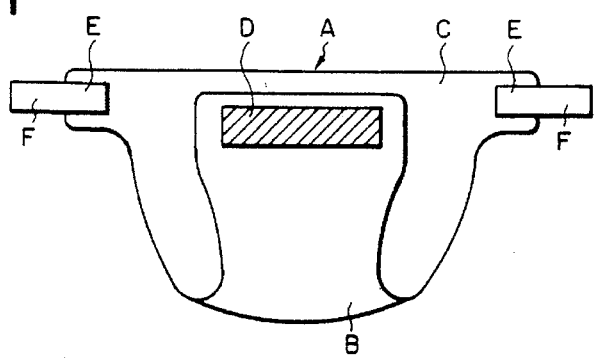
FIG. 1 is a schematic front view showing the construction of a paper diaper.

The present invention is described in more detail below.

In the present invention, in the case of releasing the the pressure-sensitive adhesive layer from the releasing agent layer at the boundary thereof in the releasing part comprising the layers, the sound pressure level in releasing at a releasing speed of at least $1\times10^2$ mm/minutes, and preferably a releasing speed of from $1\times10^2$ to $5\times10^4$ mm/minutes is 80 dB or less, and preferably from about 55 to 75 dB. If such a sound pressure level is over the above-described range, the releasing sound becomes noises to the surroundings to undesirably trouble other persons.

Furthermore, in the present invention, it is preferred that the releasing force in releasing the pressure-sensitive adhesive layer from the releasing layer at a releasing speed of at least $1\times10^2$ mm/minutes is larger than the releasing force in releasing the layer at a releasing speed of less than $1\times10^2$ mm/minute.

When the relationship between the releasing speed and the releasing force is contrary to the above relationship, a slip stick phenomenon occurs and the chart pattern of the releasing force greatly heaves, which results in undesirably increasing the releasing noises.

When the releasing force in releasing the pressure-sensitive adhesive layer from the releasing agent layer at a releasing speed of at least $1\times10^2$ mm/minute becomes largest, that is, when the releasing force is increased with the increase of the releasing speed, the slip stick phenomenon does not occur and as a result thereof, the chart pattern of the releasing force becomes moderate and the release noise becomes quiet.

It is also preferred in the present invention that the difference between the maximum value and the minimum value of the releasing force in releasing the pressure-sensitive adhesive layer from the releasing layer at a releasing speed of $1\times10^2$ mm/minute is 200 g/25 mm or less, and preferably from 10 to 100 g/25 mm, for the reasons that releasing is smoothly conducted and no vibration causes, which are effective for making soundless or noiseless.

The composition for the pressure-sensitive adhesive layer forming the boundary in the structure of the releasing part of the present invention is not particularly limited if the composition of a pressure-sensitive adhesive composition comprises a rubber-based or acrylic pressure-sensitive adhesive as a main component.

For example, a pressure-sensitive adhesive composition mainly comprising a natural rubber or a synthetic rubber can be used as the rubber-based pressure-sensitive adhesive composition. In particular, the rubber-based pressure-sensitive adhesive composition mainly comprising an ABA type block copolymer or an AB type block copolymer (wherein A is a thermoplastic block, B is a rubber block, and examples of those block copolymers are a styrene-isoprene-styrene copolymer, a styrene-butadiene-styrene copolymer, a styrene-ethylene-butadiene-styrene copolymer, a styrene-butadiene copolymer, and the hydrogenated products of those copolymers) is preferred from the standpoint of non-pollution due to hot melt coating.

There is no particular limitation on the acrylic pressure-sensitive adhesive composition, but crosslinking is frequently required for those acrylic pressure-sensitive adhesives. For example, acrylic emulsions, polyacrylic acid esters (e.g., methyl acrylate, ethyl acrylate, butyl acrylate and 2-ethylhexyl acrylate), etc., are used.

The pressure-sensitive adhesive composition is, if necessary, coated on a substrate such as a tape support, etc., to prepare the pressure-sensitive adhesive layer for the releasing part structure of the present invention or a pressure-sensitive adhesive tape having the pressure-sensitive adhesive layer.

There is no particular limitation on the thickness of the above-described pressure-sensitive adhesive layer, but the thickness is usually from 20 to 100 μm.

The releasing agent layer which is another layer of the layers forming the boundary in the releasing part structure of the present invention is a layer formed with a long chain alkyl type releasing agent or a silicone type releasing agent.

Examples of the long chain alkyl type releasing agent which can be used are Type BP (trade name, manufactured by Nitto Denko Corporation), Ashioresin (trade name, manufactured by Ashio Co., Ltd.), and Peeloil (trade name, manufactured by Ipposha Yushi Co., Ltd.). Examples of the silicone type releasing agent which can be used are silicone type releasing agents comprising dimethylsiloxane, which are usually used as releasing agents.

The above-described silicone type releasing agent which further contains a three-dimensional organopolysiloxane as disclosed in JP-A-5-17728 can be particularly preferably used in the present invention.

The amount of the releasing agent coated is usually from 0.01 to 10 g/m$^2$, and preferably from 0.1 to 3 g/m$^2$ in the case of the silicone type releasing agent, and is from 0.005 to 10 g/m$^2$, and preferably from 0.02 to 0.3 g/m$^2$ in the case of the long chain alkyl type releasing agent. However, when the pressure-sensitive adhesive agent layer comprises the acrylic type pressure-sensitive adhesive composition, it is necessary to satisfy the holding property by slightly decreasing the amount of the releasing agent coated to impart the heavy releasing property, and in this case, the coating amount is preferably from 0.01 to 0.1 g/m$^2$.

On the other hand, the releasing agent can be coated on the back surface of a releasing tape or the back surface of a reinforcing film of a paper diaper and further can be directly coated on the surface of the back sheet of the paper diaper.

There is no limitation on the film or tape as the substrate. However, the preferred examples of the substrate are the polypropylene-containing plastics as described in JP-A-63-112704, a laminate of polypropylene and a polypropylene-containing plastic, and a polyester. The surface of the substrate may be flat or a matted form. Furthermore, a foam material and a substrate having an uneven surface can be used.

Also, a plastic film comprising an olefin elastomer, a styrene elastomer, an urethane elastomer, or a polyester elastomer can be preferably used as the substrate in the present invention in the points that the film shows a good slipping property and is soft.

It is preferred that a surface treatment such as a corona discharging treatment, etc., is previously applied to the surface of the film or tape to prevent the releasing agent coated on the surface from falling off or peeling, and a surface tension of at least 38 dynes/cm$^2$ is preferred as a measure of the surface treatment strength.

The application examples utilizing the releasing part structure of the present invention are explained by referring to the accompanying drawings.

FIG. 1 is a schematic front view showing each portion of a paper diaper A, wherein B is a back sheet, C is a top sheet of a belt portion, D is a reinforcing film, E is a releasing tape, and F is a fastener tape.

Figure 2:
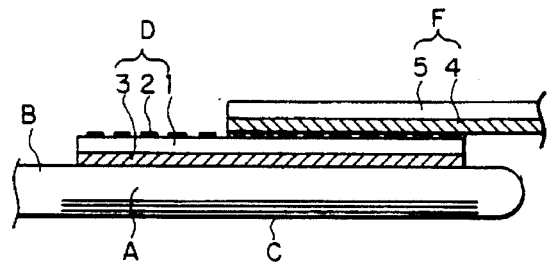
FIG. 2 is a cross sectional view showing one example of the present invention in a fastener part of a paper diaper.

FIG. 2 is a cross sectional view showing an example of the releasing part structure in the case that the releasing part structure of the present invention is applied to the connection of the reinforcing film D on the back sheet B of the paper diaper A and the fastener tape. The film having coated on the surface thereof the releasing layer 2 is bonded onto the back sheet B with an adhesive 3. On the other hand, on the releasing layer 2 of the reinforcing film D is releasably fixed the fastener tape F having the pressure-sensitive adhesive layer 4 of a pressure-sensitive adhesive composition mainly comprising a rubber-based or acrylic pressure-sensitive adhesive through the layer 4, and the releasing part structure of the present invention is formed at the boundary between the layer 2 and the layer 4.

In addition, in place of the construction described above, the film 1 having the releasing layer 2 on the surface may be directly heat-adhered on the back sheet B or the releasing agent used in the present invention may be directly coated on the back sheet B of the paper diaper A.

Figure 3:
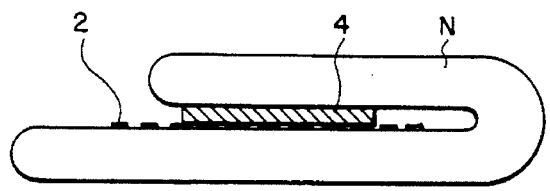
FIG. 3 is a schematic cross sectional view showing another application example of the present invention.

FIG. 3 is a schematic cross sectional view showing an example that the fixing structure (releasing part structure) of the present invention is applied to a sanitary napkin.

As shown in FIG. 3, a pressure-sensitive adhesive layer 4 comprising a pressure-sensitive adhesive composition is formed on the inside surface of an end portion of the napkin N, on the other hand, a releasing agent layer 2 comprising the releasing agent is formed by coating on the inside surface of the other end of the napkin N, and the napkin N is bent such that the pressure-sensitive adhesive layer 4 is contacted with the upper surface of the releasing agent layer 2 to constitute the releasing part structure of the present invention at the boundary between the layer 2 and the layer 4.

Figure 4:
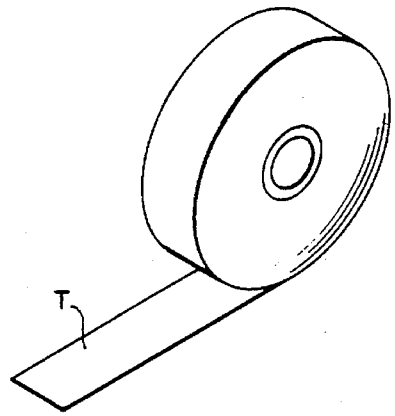
FIG. 4 is a perspective view showing an example of applying the fixing structure of the present invention to a roll-form tape.

FIG. 4 is a perspective view showing an example of applying the fixing structure of the present invention to a roll-form tape T.

The pressure-sensitive adhesive layer (not shown) is formed on the inside surface of the tape T and on the other hand, the releasing agent layer (not shown) is formed on the back surface of the tape T. Thus, in the rolled state of the tape T, the pressure-sensitive adhesive layer is contacted with the releasing agent layer at the boundary of those layers of the rolled tape to constitute the releasing part structure of the present invention at the boundary.

Figure 5:
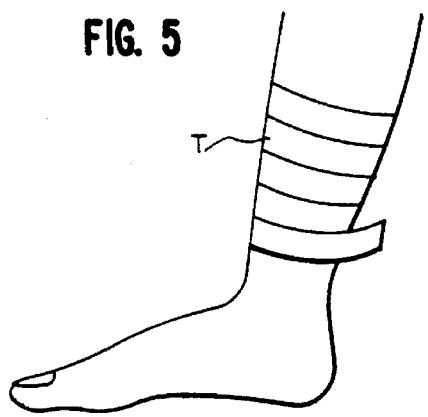
FIG. 5 is a schematic view showing an example of applying the present invention to a medical tape.
Figure 6:
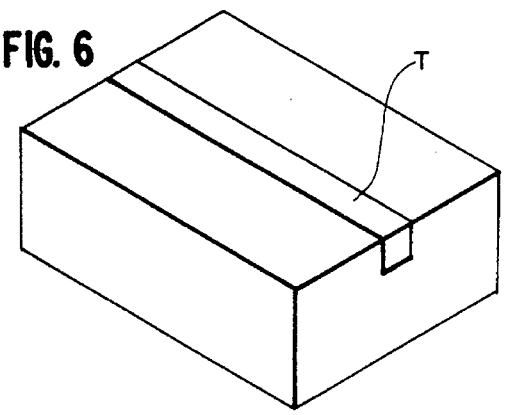
FIG. 6 is a schematic view showing an example of applying the present invention to a packing tape.

FIG. 5 and FIG. 6 are views showing examples that the roll-form tape T is applied to a medical tape and a packing tape for a corrugated board.

As shown in FIG. 5, by winding the tape T while lapping the tape, the releasing part structure of the present invention is similarly constituted at the lapped portions. Also, as shown in FIG. 6, the releasing agent is previously coated (not shown) on the sealing portions of the corrugated board and the tape T (in this case, the releasing agent layer of the tape T may not be formed) is attached to seal the sealing portions, whereby the releasing part structure of the present invention is similarly obtained.

The present invention is explained in more detail by the following examples, in which "%" and "parts" are "by weight".

Preparation of a Material to be Adhered
(Reinforcing Film)

A solution prepared by mixing a toluene solution (30% as solid content) of an addition type silicone resin (X-62-2378, trade name, manufactured by Shin-Etsu Chemical Co., Ltd.) and a toluene/xylene solution (30% as solid content) of a three-dimensional organopolysiloxane (X-92-140, trade name, manufactured by Shin-Etsu Chemical Co., Ltd.) such that the content of the three-dimensional organopolysiloxane became 30% was coated on a polyester (PET) film having a thickness of 12 μm at 0.38 g/m² as a silicone type releasing agent and was heated to 120° C. for one minute to form a releasing layer, thereby obtaining a material 1 to be adhered.

A 2% toluene solution of a long chain alkyl type releasing agent (Peeloil 1010, trade name, manufactured by Ipposha Yushi Co., Ltd) was coated on an oriented polypropylene (OPP) film having a thickness of 25 μm at 0.02 g/m² and dried at 80° C. for one minute to form a releasing agent layer, thereby obtaining a material 2 to be adhered.

Preparation of Pressure-Sensitive Adhesive Tape
(Fastener Tape)

Each of the pressure-sensitive adhesive compositions shown below was coated on one surface of a low-density polyethylene film having a thickness of 120 μm at a thickness of 50 μm each to form a pressure-sensitive adhesive layer, thereby obtaining each pressure-sensitive adhesive tape.

EXAMPLE 1

Compounding of Pressure-Sensitive Adhesive

| | |
|---|---|
| Synthetic Rubber SIS (JSR-5500, trade name, made by Japan Synthetic Rubber Co., Ltd.) | 100 parts |
| Petroleum Resin (Super Ester, trade name, made by Arakawa Chemical Industries, Ltd.) | 100 parts |
| Antioxidant (Irganox 1010, trade name, made by Ciba-Geigy Limited) | 2 parts |

The above components were compounded and coated as described above.

The pressure-sensitive adhesive tape thus obtained was adhered to the releasing agent layer of the material 1 to obtain the releasing part structure of the present invention.

EXAMPLE 2

Compounding of Pressure-Sensitive Adhesive

| | |
|---|---|
| Synthetic Rubber SIS (JSR-5500, trade name, made by Japan Synthetic Rubber Co., Ltd.) | 100 parts |
| Petroleum Resin (Kraton N-130, trade name, made by Japan Synthetic Rubber Co., Ltd.) | 100 parts |
| Softening Agent (YS-Resin TOS, trade name, made by Yasuhara Yushi Kogyo Co., Ltd.) | 50 parts |
| Antioxidant (Irganox 1010, trade name, made by Ciba-Geigy Limited) | 2 parts |

The above components were compounded and coated as described above.

The pressure-sensitive adhesive tape thus obtained was adhered to the releasing agent layer of the material 1 to obtain the releasing part structure of the present invention.

EXAMPLE 3 (Acrylic Pressure-Sensitive Adhesive)

Compounding of Pressure-Sensitive Adhesive

| | |
|---|---|
| Copolymer of 2-Ethylhexyl Acrylate and Acrylic Acid (100/2 by weight ratio) | 100 parts |
| Isocyanate Type Crosslinking Agent (Colonate L, trade name, made by Nippon Polyurethane Kogyo Co., Ltd.) | 1 part |

The above components were compounded and coated as described above.

The pressure-sensitive adhesive tape thus obtained was adhered to the releasing agent layer of the material 2 to obtain the releasing part structure of the present invention.

COMPARATIVE EXAMPLE

A pressure-sensitive adhesive tape using the same composition of the pressure-sensitive adhesive as shown in Example 1 was prepared and adhered to the releasing agent layer of the material 2 to provide a releasing part structure.

Figure 7:
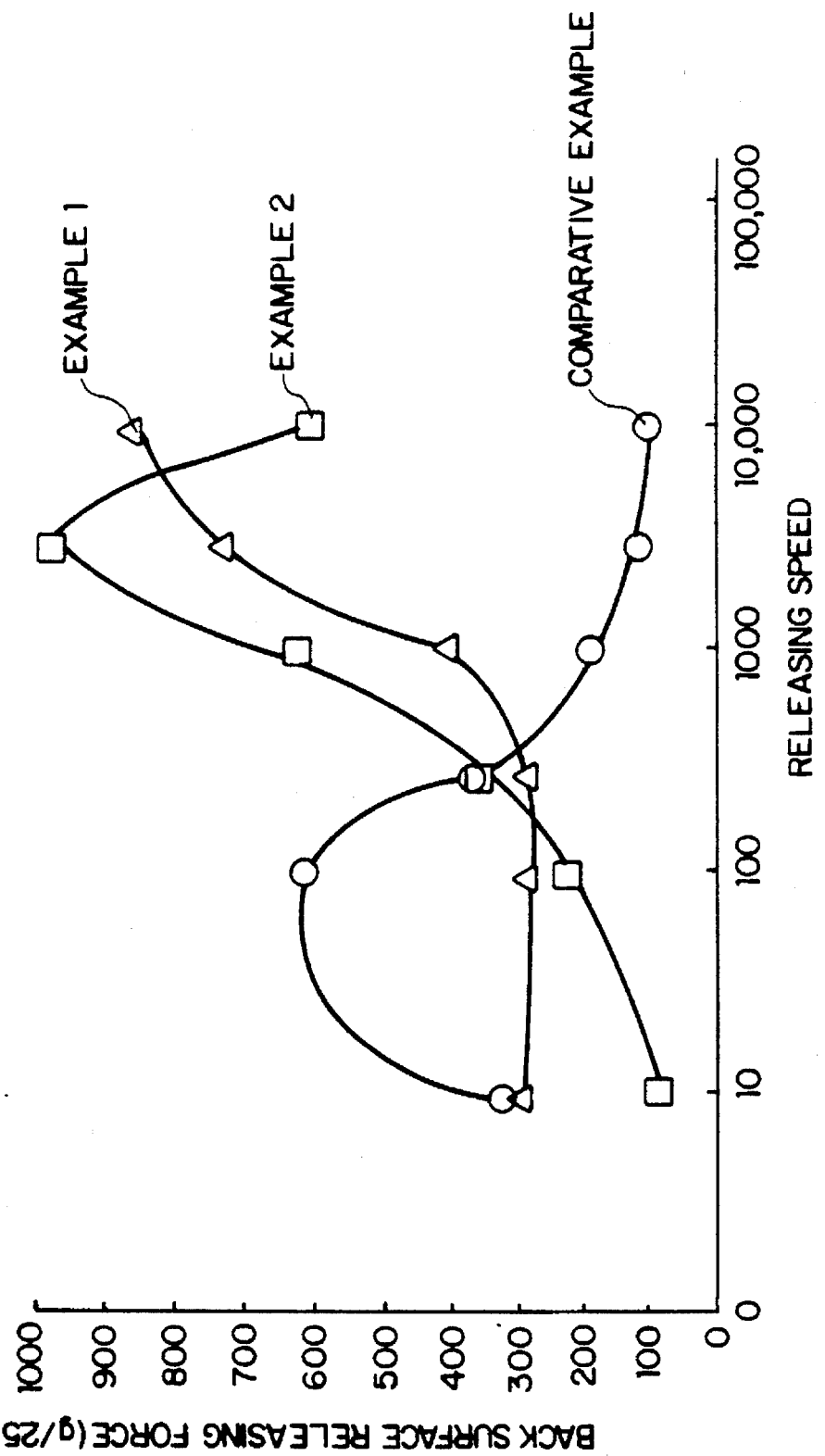
FIG. 7 is a graph of the data showing each releasing speed dependence of the back surface releasing force in the examples of the present invention.
Figure 9D:
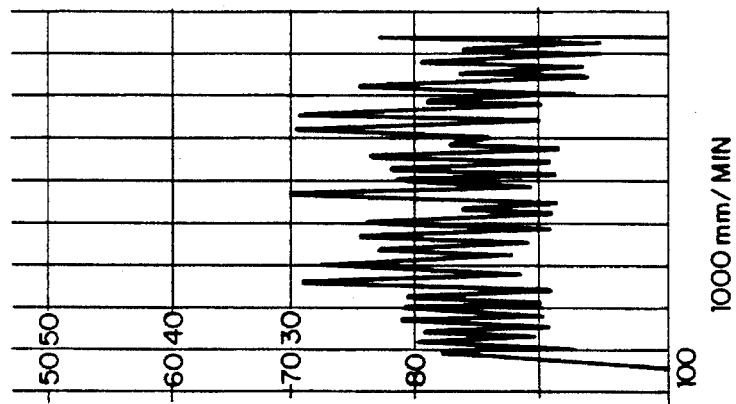
FIG. 9 is a graph of the pattern showing the back surface releasing force in the various releasing speeds in the comparative example.
Figure 9C:
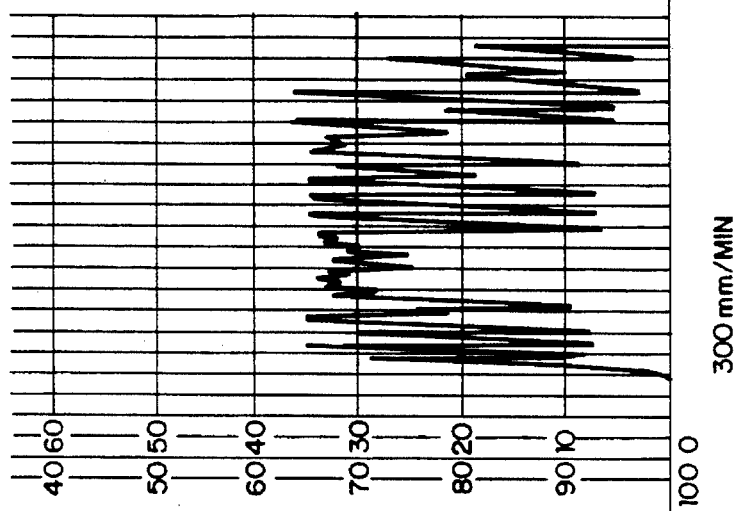
Figure 9B:
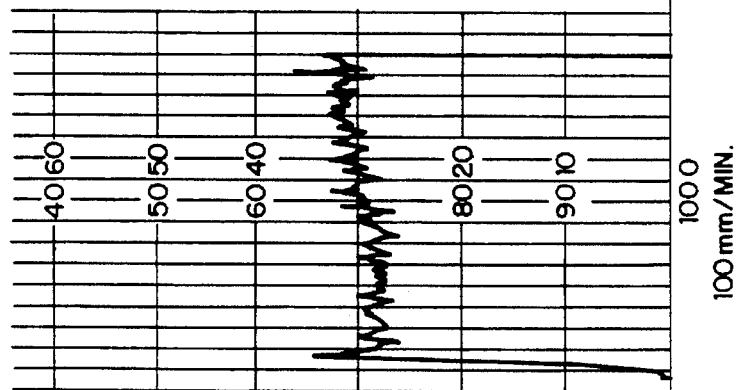
Figure 9A:
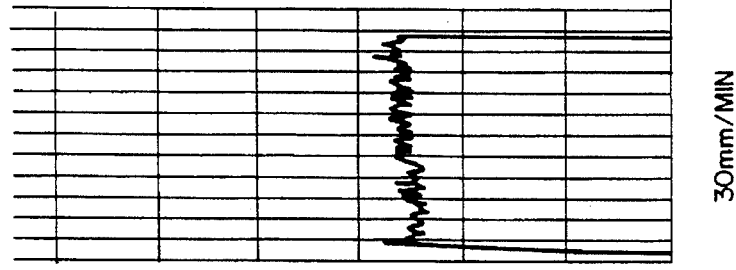

For each of the releasing part structures formed above, the releasing speed dependence was measured and the results are shown in FIG. 7.

As is clear from the results shown in FIG. 7, it can be seen that when the pressure-sensitive adhesive layer is released from the releasing agent layer, the sound pressure level is small in the case that the releasing force in releasing the pressure-sensitive adhesive layer at a releasing speed of at least $1\times10^2$ mm/minute is larger than the releasing force in releasing the layer at a releasing speed lower than $1\times10^2$ mm/minute. Further, it can be seen that when the releasing force in releasing the pressure-sensitive adhesive layer at a releasing speed of at least $1\times10^2$ mm/minute is largest, the sound pressure level is also small.

The chart patterns of the back surface releasing forces at various releasing speeds for each releasing part structure are shown in FIG. 8 (Example 1) and FIG. 9 (Comparative Example). The differences between the maximum value and the minimum value of each releasing force are shown in Table 1 below.

Furthermore, the results of the sound pressure level of the releasing sound or noise in each releasing part structure are shown in Table 1 below.

TABLE 1

|  | Example 1 | Example 2 | Example 3 | Comparative Example |
|---|---|---|---|---|
| Difference between the maximum value and the minimum value in releasing force (g/25 mm) Releasing speed |  |  |  |  |
| $10^3$ mm/min | 90 | 132 | 100 | 480 |
| $10^2$ mm/min | 60 | 95 | 80 | 200 |
| Sound Pressure Level (dB) | 55–70 | 75–80 | 60–75 | 85–90 |

Each value was measured by the following method.

Releasing Force

Each sample piece having each releasing agent layer was fixed on a stainless steel plate, the pressure-sensitive adhesive layer of a sample piece of each pressure-sensitive adhesive tape was adhered to the releasing agent layer of the sample piece fixed on the stainless steel plate by one reciprocating movement of a roller of 2 kg, and within 3 minutes after adhering, the releasing force at each releasing speed was measured.

Chart Pattern

In measuring the above-described releasing force, the releasing force was recorded by Tensilon.

Measurement Method of Sound Pressure Level

Each of the materials to be adhered was adhered to a commercially available paper diaper and the pressure-sensitive adhesive tape in the present invention was press-adhered to the releasing agent layer of the material to be adhered by one reciprocating movement of a roller of 700 g. Within 3 minutes after adhered, the pressure-sensitive adhesive tape was released at a releasing speed of from 10 mm/minute to 50 m/minute, and the releasing sound at initial releasing was measured at a measurement distance of 100 mm using a precision integrating sound level meter. In addition, in this case, when the blank decibel of the surrounding was measured, it was confirmed to be 50 dB.

As described above, the releasing part structure of the present invention has the characteristic that a member such as a tape is reluctant to release at fixing and on the other hand, the member is easily released in releasing without making noise. Accordingly, the releasing part structure of the present invention is useful as the formation of the releasing parts of a paper diaper, etc., as releasing part structures of disposable absorptive articles aiming other releasable fixing, and also as releasing part structures of life relating articles such as medical tapes, packing tapes, etc.

In particular, the releasing part structure of the present invention, which can be used to fix a paper diaper that is capable of releasing without making sound and noise, has a large value of the practical use thereof for meeting the consumers' demand, at present of increasing the popularization of paper diapers using a large amount of paper diapers, and further increasing the frequency of using at midnight.

The invention was explained in the case of using mainly the releasing part structure of a diaper, but the releasing part structure of the present invention can be also used as the releasing part structures of other disposable absorptive articles such as sanitary napkins and also suitable for use as releasing part structures using medical tapes in hospitals without disturbing sleeping of other patients at midnight. Also, the present invention is useful as the releasing part structures of corrugated boards using packing tapes which are largely used and releasing part structures of other various life relating articles since the releasing sounds or noises are reduced.

Furthermore, in general, in a roll-form tape, a releasing part is constituted between rolled layers of the tape and when the releasing part structure of the present invention is applied to the structure, the releasing sound at unrolling the rolled tape is reduced and hence the present invention is effective to improve surroundings with releasing noises in a workshop.

While the invention has been described in detail and with reference to specific embodiments thereof, it will be apparent to one skilled in the art that various changes and modifications can be made therein without departing from the spirits and scope thereof.

What is claimed is:

1. A releasing part structure having a boundary component, wherein said boundary component comprises a pressure-sensitive adhesive layer and a long chain alkyl releasing agent layer, wherein said pressure-sensitive adhesive layer comprises a pressure-sensitive adhesive composition comprising an acrylic pressure-sensitive adhesive, wherein when the pressure-sensitive adhesive layer is released from the releasing agent layer, the sound pressure level in releasing the pressure-sensitive adhesive layer from the releasing agent layer at all releasing speeds of at least $1\times10^2$ mm/minute is 80 Db or less and the difference between the maximum value and the minimum value of the releasing force in releasing at a releasing speed of $1\times10^2$ mm/minute is 200 g/25 mm or less.

2. The releasing part structure of claim 1, wherein in the case of releasing the pressure-sensitive adhesive layer from the releasing agent layer, the releasing force in releasing at all releasing speeds of at least $1\times10^2$ mm/minute is larger than the releasing force in releasing at all releasing speeds of lower than $1\times10^2$ mm/minute.

3. The releasing part structure of claim 1, wherein in the case of releasing the pressure-sensitive adhesive layer from the releasing agent layer, the releasing force is at its highest value at a releasing speed of at least $1\times10^2$ mm/minute.

4. The releasing part structure of claim 1, wherein the boundary component which comprises the pressure-sensitive adhesive layer and the releasing agent layer is formed by a member constituting a diaper or a napkin.

* * * * *